US010603540B2

(12) United States Patent
Ikeda et al.

(10) Patent No.: US 10,603,540 B2
(45) Date of Patent: Mar. 31, 2020

(54) TONGUE PRESSURE STRENGTHENING TRAINING DEVICE AND TONGUE PRESSURE STRENGTHENING TRAINING METHOD

(71) Applicants: JMS Co., Ltd., Hiroshima-shi, Hiroshima (JP); HIROSHIMA UNIVERSITY, Higashi-Hiroshima-shi, Hiroshima (JP)

(72) Inventors: Noboru Ikeda, Tokyo (JP); Yoshihiro Yoshiike, Tokyo (JP); Daiki Aruga, Tokyo (JP); Koichiro Toyota, Hiroshima (JP); Kazuhiro Tsuga, Hiroshima (JP)

(73) Assignees: JMS Co., Ltd. (JP); HIROSHIMA UNIVERSITY (JP)

( * ) Notice: Subject to any disclaimer, the term of this patent is extended or adjusted under 35 U.S.C. 154(b) by 58 days.

(21) Appl. No.: 15/563,336

(22) PCT Filed: Mar. 30, 2016

(86) PCT No.: PCT/JP2016/060430
§ 371 (c)(1),
(2) Date: Sep. 29, 2017

(87) PCT Pub. No.: WO2016/159100
PCT Pub. Date: Oct. 6, 2016

(65) Prior Publication Data
US 2018/0064989 A1    Mar. 8, 2018

(30) Foreign Application Priority Data

Mar. 31, 2015 (JP) ................................ 2015-074602

(51) Int. Cl.
*A61B 5/00* (2006.01)
*A63B 23/03* (2006.01)
(Continued)

(52) U.S. Cl.
CPC .............. *A63B 23/032* (2013.01); *A61B 5/11* (2013.01); *A61B 5/4552* (2013.01); *A63B 23/03* (2013.01);
(Continued)

(58) Field of Classification Search
None
See application file for complete search history.

(56) References Cited

U.S. PATENT DOCUMENTS 4,133,306 A    1/1979  Berry
4,296,756 A *  10/1981 Dunning .................. A61B 5/08
                                                   600/529

(Continued)

FOREIGN PATENT DOCUMENTS

CN    2361326 Y    2/2000
JP    2004-129817 A   4/2004
(Continued)

OTHER PUBLICATIONS

Supplementary European Search Report for Patent Application No. EP16772981.3, dated Sep. 24, 2018 (7 pages).
(Continued)

*Primary Examiner* — Etsub D Berhanu
(74) *Attorney, Agent, or Firm* — Harness, Dickey & Pierce, P.L.C.

(57) ABSTRACT

A device includes: a controller that converts a pressure value detected by a pressure detector into visual or aural lingual pressure information changed depending on a magnitude of the pressure value; and an information output unit, such as a buzzer and a color display LED, that outputs the lingual pressure information in response to a signal from the controller. The information output unit outputs lingual pressure information different depending on a pressing force applied on an elastic balloon by a tongue, allowing users such as (Continued)

patients and elderly people to continue a training without being bored.

6 Claims, 10 Drawing Sheets

(51) Int. Cl.
*A61B 5/11* (2006.01)
*A63B 71/06* (2006.01)
*A61B 5/22* (2006.01)

(52) U.S. Cl.
CPC ......... *A63B 71/0622* (2013.01); *A61B 5/1127* (2013.01); *A61B 5/228* (2013.01); *A61B 5/682* (2013.01)

(56) References Cited

U.S. PATENT DOCUMENTS

| | | | |
|---|---|---|---|
| 5,452,727 A | | 9/1995 | Tura et al. |
| H001557 H | * | 7/1996 | Joubert .................. 128/905 |
| 5,647,375 A | * | 7/1997 | Farfan de los Godos ................. A61B 5/103 600/594 |
| 5,941,828 A | * | 8/1999 | Archibald .......... A61B 5/02116 600/494 |
| 6,088,606 A | * | 7/2000 | Ignotz .................. A61B 3/10 600/316 |
| 2003/0078521 A1 | * | 4/2003 | Robbins ................ A61B 5/228 600/587 |
| 2008/0183107 A1 | | 7/2008 | Miller et al. |
| 2010/0090859 A1 | | 4/2010 | Sato et al. |
| 2010/0222706 A1 | | 9/2010 | Miyahara et al. |
| 2011/0043357 A1 | | 2/2011 | Peatfield et al. |
| 2011/0190666 A1 | | 8/2011 | Friedland et al. |
| 2013/0296751 A1 | | 11/2013 | Martin et al. |
| 2014/0066258 A1 | * | 3/2014 | Smead .................. A63B 21/02 482/11 |
| 2014/0073900 A1 | * | 3/2014 | Wood .................. A61B 5/0095 600/407 |

FOREIGN PATENT DOCUMENTS

| | | |
|---|---|---|
| JP | 2005-013679 A | 1/2005 |
| JP | 2008-110024 A | 5/2008 |
| JP | 2014-155655 A | 8/2014 |
| TW | 201228638 A | 7/2012 |
| WO | WO-2007-026488 A1 | 3/2007 |

OTHER PUBLICATIONS

Chinese Office Action for Patent Application No. CN 201680020263.6 dated Dec. 18, 2018 (11 pages).
Report of Results of Reconsideration for corresponding Japanese Patent Application No. 2015-074602 dated Jun. 18, 2019 with English translation (5 pages).
Japanese Office Action for Application No. 2019-085602, dated Jan. 28, 2020 (4 pages).

* cited by examiner

TONGUE PRESSURE STRENGTHENING TRAINING DEVICE AND TONGUE PRESSURE STRENGTHENING TRAINING METHOD

BACKGROUND

Technical Field

The present invention relates to a lingual pressure strengthening training device and a lingual pressure strengthening training method.

Background Art

A lingual pressure measuring device with a training function may be used by a patient or an elderly person whose eating/swallowing function is impaired in order to restore his or her eating/swallowing function. Such a device with the training function is usable for not only training but also measuring a lingual pressure.

An example of a typical lingual pressure measuring device with a training function is a rehabilitation tool including: a frame member; an insertion unit attached to the frame member and provided with an elastic balloon that is to be inserted in a mouth; a grip provided to the frame member; and a tubular member having a first end connected to the elastic balloon and a second end connected to a lingual pressure measuring device (JP 2008-110024 A).

The lingual pressure measuring device of the rehabilitation tool of JP 2008-110024 A includes a pressure detector and a controller, and a pressure value detected by the pressure detector is sent to the controller in the form of an electrical signal. The controller controls a display to show the detected pressure value thereon.

When a patient or an elderly person pushes the elastic balloon of the rehabilitation tool of JP 2008-110024 A with his or her tongue, a pressure value detected by the pressure detector appears on the display.

Rehabilitation is a monotonous activity for patients and elderly people. Further, doing rehabilitation while checking the pressure value appearing on the display will bore patients or elderly people. Accordingly, the rehabilitation tool of JP 2008-110024 A, which cannot provide enough changes for patients or elderly people to do a lingual pressure strengthening training while having fun, may fail to give a motivation for continuing the training for a long time.

An object of the invention is to provide a lingual pressure strengthening training device and a lingual pressure strengthening training method that allow a user to do a training while having fun.

SUMMARY

According to an aspect of the invention, a lingual pressure strengthening training device includes: an elastic balloon configured to be inserted in a mouth; a pressure detector configured to detect an internal pressure of the elastic balloon; a controller configured to convert a pressure value detected by the pressure detector into at least one of visual lingual pressure information and aural lingual pressure information, the at least one of visual lingual pressure information or aural lingual pressure information being variable depending on the pressure value; and an information output unit configured to output the lingual pressure information in response to a signal from the controller.

According to the invention, the visual lingual pressure information refers to visually recognizable information such as letter, graphic, number, graph and color and the aural lingual pressure information refers to aurally recognizable lingual pressure information such as music, alarm and any other sound.

In the above aspect, a user such as a patient and an elderly person inserts the elastic balloon between his or her palate and tongue, presses the elastic balloon against his or her palate with his or her tongue, and stops pressing the elastic balloon with his or her tongue. Such a motion of the tongue is repeated to perform the lingual pressure strengthening training. When a large pressing force is applied on the elastic balloon by the tongue, the internal pressure of the elastic balloon becomes high. The resulting pressure value is detected by the pressure detector and sent to the controller. The controller controls the information output unit to output the lingual pressure information. When the user stops pressing the elastic balloon with his or her tongue, the internal pressure of the elastic balloon drops. In contrast, when a small pressing force is applied on the elastic balloon by the tongue, the internal pressure of the elastic balloon becomes low. The pressure detector thus detects a small pressure value, which is sent to the controller. The controller controls the information output unit to output lingual pressure information different from the lingual pressure information for a large pressure value.

The information output unit thus outputs the lingual pressure information different depending on the pressing force applied on the elastic balloon by the tongue, allowing users such as patients and elderly people to continue a training without being bored.

In the above aspect, it is preferable that the lingual pressure information is represented by at least a color.

The information output unit thus outputs a color changed depending on the pressing force applied on the elastic balloon by the tongue, making the lingual pressure visually recognizable. Such a change in color allows patients or elderly people, especially hearing-impaired people, to train while having fun.

In the above aspect, it is preferable that the color representing the lingual pressure information includes first and second opposite colors, and the controller is configured to control the information output unit to display the first opposite color when the pressure value detected by the pressure detector is equal to or more than a reference value, and to display the second opposite color when the pressure value detected by the pressure detector is less than the reference value.

According to the invention, opposite colors refer to not only two colors (complementary colors) opposite to each other in a color circle but also colors slightly deviated from such two colors. For instance, red and green are complementary colors while red and blue are opposite colors.

The above arrangement allows the information output unit to output the first opposite color, such as blue whose impression is "safety", when the pressing force applied on the elastic balloon by the tongue is equal to or more than the reference value, and allows the information output unit to output the second opposite color, such as red whose impression is "danger", when the pressing force is less than the reference value. The patient or elderly person is thus motivated to forcefully press the elastic balloon so that, for instance, blue is displayed, thereby efficiently strengthening the lingual pressure.

In the above aspect, it is preferable that the lingual pressure information is represented by a sound.

The above arrangement allows the information output unit to output a sound changed depending on the pressing force applied on the elastic balloon by the tongue, making the lingual pressure aurally recognizable. Such a change in sound allows patients or elderly people, especially blind people, to train while having fun.

In the above aspect, it is preferable that the controller is configured to control the information output unit to make the sound with a pitch increased in proportion to the pressure value detected by the pressure detector.

The above arrangement can melodiously change a sound depending on the pressing force applied on the elastic balloon by the tongue, allowing patients or elderly people to continue the lingual pressure strengthening training without being bored.

According to another aspect of the invention, a lingual pressure strengthening training method includes: inserting an elastic balloon in a mouth; pressing the elastic balloon with a tongue; detecting an internal pressure of the pressed elastic balloon with a pressure detector; and outputting at least one of visual lingual pressure information and aural lingual pressure information with an information output unit, the at least one of visual lingual pressure information and aural lingual pressure information being changed depending on a magnitude of a pressure value detected by the pressure detector.

The above aspect can provide the same advantages as those described above.

BRIEF DESCRIPTION OF DRAWING(S)

DETAILED DESCRIPTION

An exemplary embodiment of the invention will be described below with reference to the attached drawings.

Figure 1:
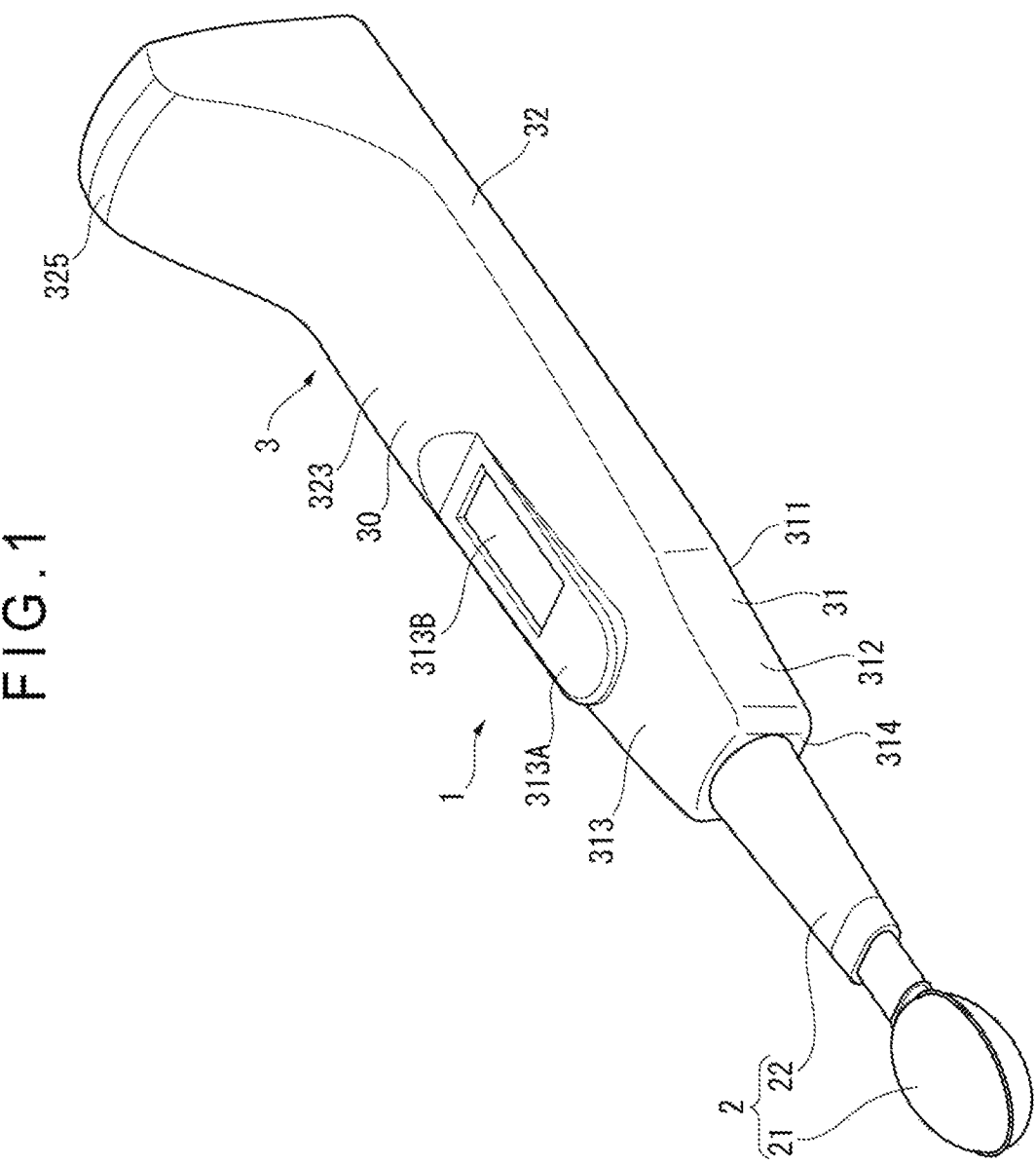
FIG. 1 is a perspective view showing a lingual pressure strengthening training device according to an exemplary embodiment of the invention.

FIG. 1 shows an overall arrangement of a lingual pressure strengthening training device of the exemplary embodiment. The lingual pressure strengthening training device of the exemplary embodiment serves also as a lingual pressure measuring device for training.

As shown in FIG. 1, the lingual pressure strengthening training device includes a device body 1 and an elastic balloon 2 provided to the device body 1.

The elastic balloon 2, which has a restoring force, includes a balloon body 21 configured to be inserted in a mouth and a tube 22 having an end connected to the balloon body 21. Air is to be introduced into the elastic balloon 2 through an opening of a base end of the tube 22.

Figure 2:
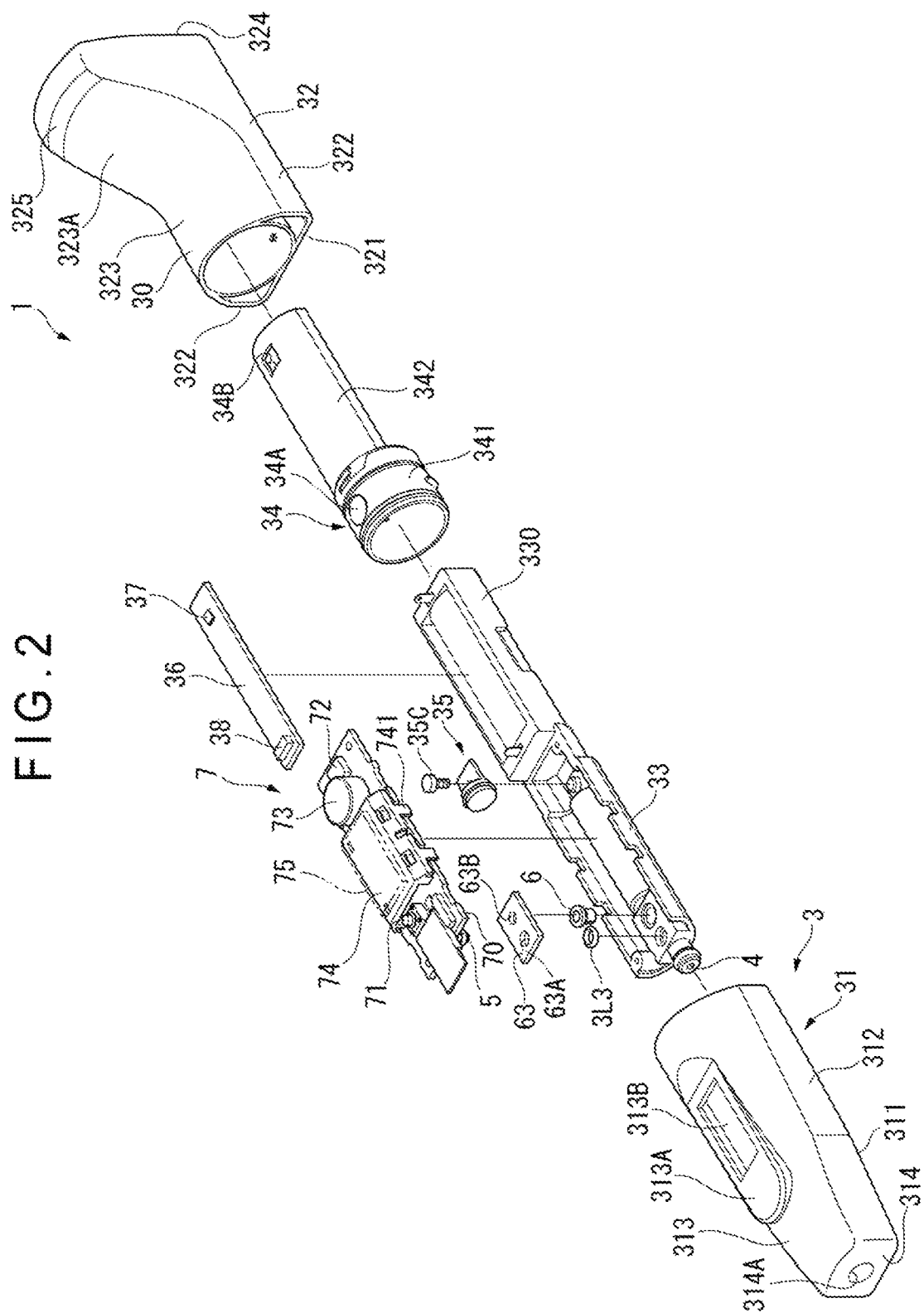
FIG. 2 is an exploded perspective view showing a device body.
Figure 3:
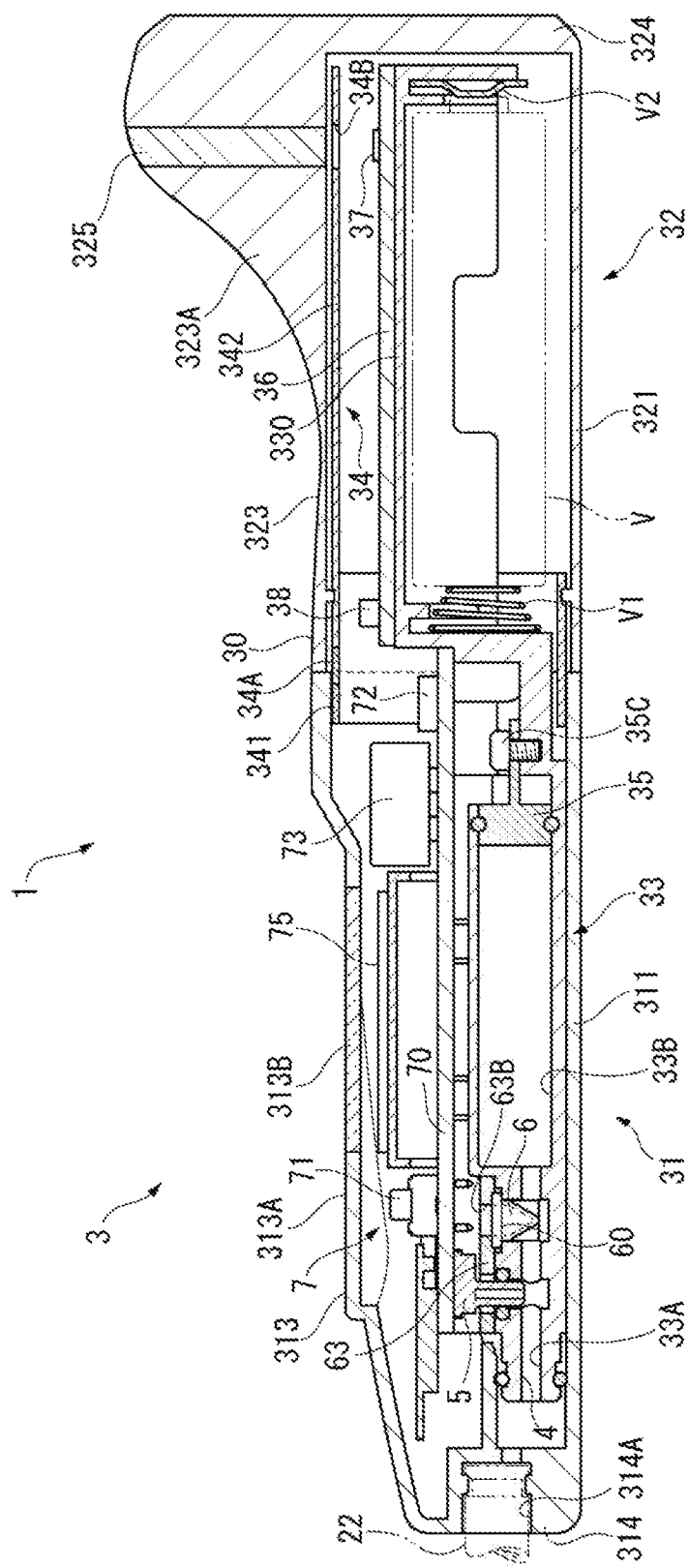
FIG. 3 is a cross sectional view showing the device body.
Figure 4:
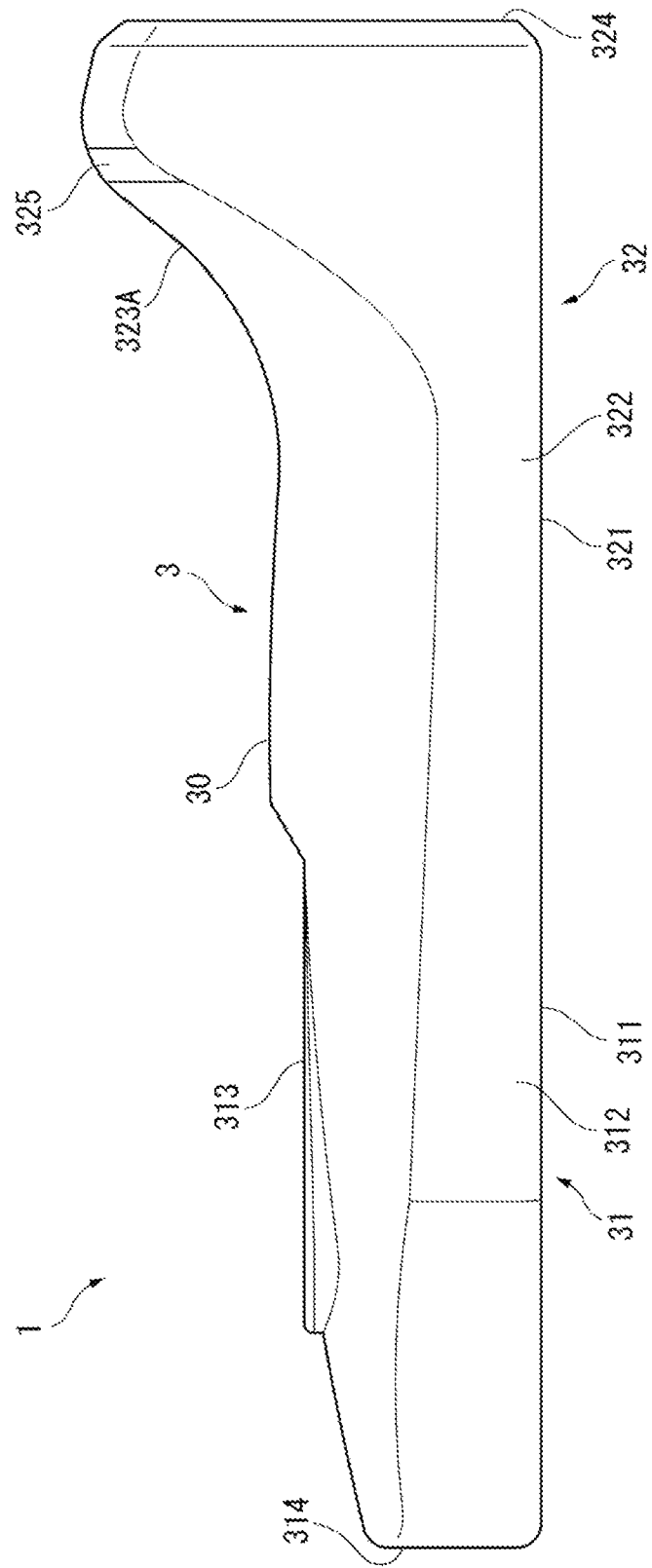
FIG. 4 is a side view showing the device body.

FIGS. 2 to 4 show an overall arrangement of the device body 1.

As shown in FIGS. 2 to 4, the device body 1 includes a casing 3.

The casing 3 includes a synthetic resin front case 31 connected to the tube 22 and a synthetic resin rear case 32 connected to the front case 31. The front case 31 and the rear case 32 are detachably attached to each other.

An inner case 33 and a ring-shaped case 34, which are made of synthetic resin, are housed respectively in the front case 31 and the rear case 32.

The front case 31 includes a plate-shaped back face 311, lateral faces 312 standing upright from both sides of the back face 311, a front face 313 connected to the lateral faces 312 and opposite to the back face 311, and an end face 314 closing a first end opening defined by the back face 311, the lateral faces 312 and the front face 313. The end face 314 is provided with a communication opening 314A configured to communicate with the tube 22. The elastic balloon 2 is removably attached to the communication opening 314A.

The front face 313, which is inclined from the first end provided with the end face 314 toward an opposite second end opening, has at a center thereof a display area 313A parallel with the back face 311. The display area 313A is provided at a center thereof with a window 313B in a rectangular shape in a plan view.

The lateral faces 312 are getting converged from middle positions thereof toward the end face 314.

The rear case 32 includes a back face 321 coplanar with the back face 311, lateral faces 322 continuous with the lateral faces 312, a front face 323 continuous with the front face 313, and a bottom face 324 provided to an opening defined by the back face 321, the lateral faces 322 and the front face 323.

The bottom face 324 has a larger area than that of the end face 314 so that the casing 3 can stand on its own when the bottom face 324 is placed on a mount surface (not shown). Accordingly, the lateral faces 322 each have a width getting larger toward the bottom face 324, and the front face 323 includes a projection 323A projecting from a surface continuous with the front case 31.

The projection 323A is provided with a light-transmitting portion 325 that allows light emitted from a color display LED 37 (described later) to be externally visible. The light-transmitting portion 325 is made of synthetic resin.

A portion of the rear case 32 other than the projection 323A is continuous with a portion of the front case 31 between the window 313B and the rear case 32. Such a continuous portion serves as a grip 30 for a user to hold by hand. A user who holds the grip by hand can easily see light transmitted through the light-transmitting portion 325.

Figure 5:
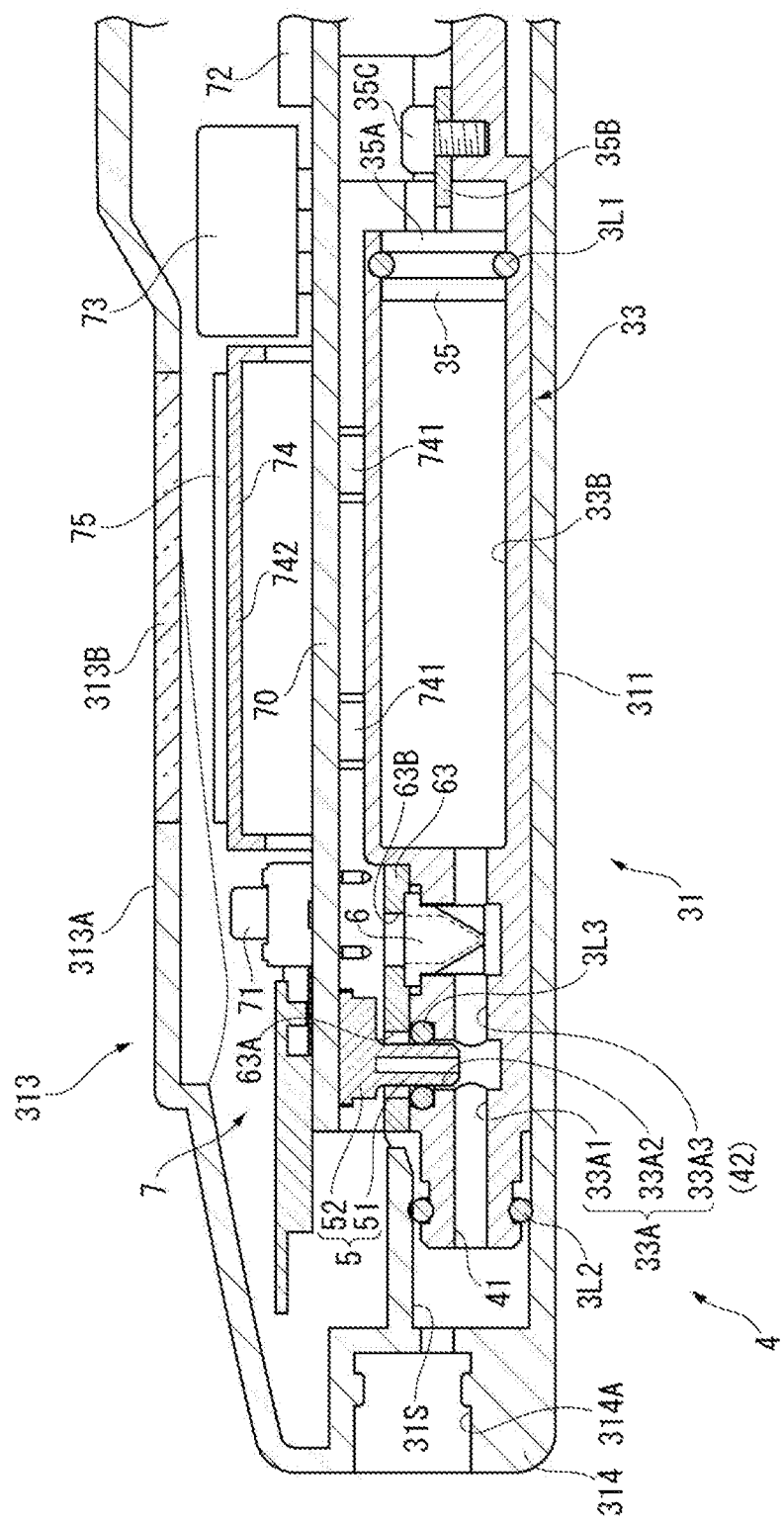
FIG. 5 is a cross sectional view showing a relevant part of the device body.

FIG. 5 shows an enlarged cross sectional view of a relevant part of the device body 1.

As shown in FIG. 5, a small-diameter hole 33A and a large-diameter hole 33B are defined inside the inner case 33, the small-diameter hole 33A having a first end whose opening communicates with the communication opening 314A and a second end that communicates with the large-diameter hole 33B.

The small-diameter hole 33A includes a first hole 33A1 that communicates with the communication opening 314A, a second hole 33A2 bent from an end of the first hole 33A1, and a third hole 33A3 connected to the end of the first hole 33A1 and aligned with the first hole 33A1.

A pressure detector 5 is located in the second hole 33A2. A check valve 6 is located in a middle of the third hole 33A3.

An end of the third hole 33A3 is in communication with the large-diameter hole 33B. An end opening of the large-diameter hole 33B opposite to the third hole 33A3 of the large-diameter hole 33B is provided with a filler plug 35 configured to hermetically close the inside of the front case 31 in conjunction with an O-ring 3L1. In other words, the large-diameter hole 33B serves as a tank configured to regulate an internal pressure of a communication channel 4.

The filler plug 35 includes a plug body 35A and an attachment piece 35B provided to the plug body 35A. The attachment piece 35B is attached to the inner case 33 with a screw 35C.

It should be noted that the tank may be provided by attaching a cylindrical member with a closed end to the inner case 33 in the exemplary embodiment.

The front case 31 has an inner space 31S that communicates with the communication opening 314A. The inner space 31S is hermetically closed by an O-ring 3L2 provided to an end of the inner case 33.

In the exemplary embodiment, the communication channel 4, which communicates with the elastic balloon 2, is defined by the inner space 31S of the front case 31 and the small-diameter hole 33A. Further, a first channel 41, which has an end opened to the pressure detector 5, is defined by the inner space 31S, the first hole 33A1 and the second hole 33A2, and a second channel 42 is defined by the third hole 33A3.

The pressure detector 5, which is a pressure sensor element provided to the inner case 33, includes a cylindrical portion 51 and a diaphragm 52.

The cylindrical portion 51 is fitted in the second hole 33A2 via an O-ring 3L3. The diaphragm 52 projects from the inner case 33.

The diaphragm 52 sends a signal detected in response to the internal pressure of the communication channel 4 to an electronic component unit 7.

Figure 6A:
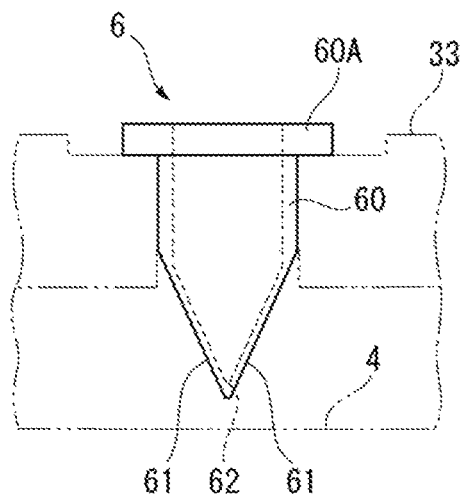
FIG. 6A is a front view showing a check valve.
Figure 6B:
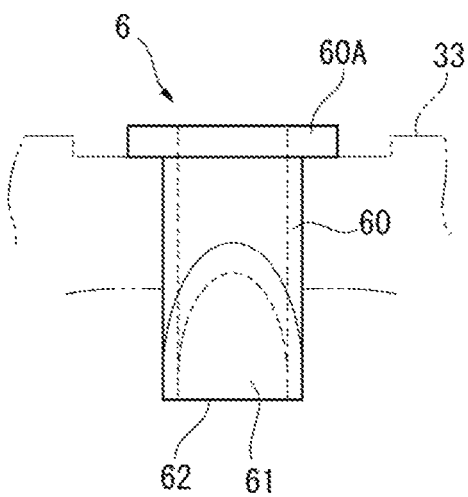
FIG. 6B is a side view showing the check valve.

FIGS. 6A and 6B show a relevant part of the check valve 6 according to the exemplary embodiment.

FIGS. 6A and 6B show the check valve 6 as it is seen in different directions.

As shown in FIGS. 6A and 6B, the check valve 6, which is formed of a duckbill valve, includes a cylindrical member 60 fitted in a hole provided to the inner case 33 and a pair of slant lips 61 integral with the cylindrical member 60.

The cylindrical member 60 has an end provided with a large-diameter portion 60A for positioning the check valve 6 to the inner case 33.

The pair of slant lips 61 extend to converge from their base ends bordering on the cylindrical member 60 toward their distal ends. Abutting surfaces at the distal ends of the pair of slant lips 61 are provided with a slit 62. The pair of slant lips 61 regulate a flow of air from the distal ends towards the base ends.

The cylindrical member 60 of the check valve 6 is opened to an inner space of the casing 3, and the inner space of the casing 3 is in communication with the atmosphere. The distal ends of the slant lips 61 face the communication channel 4.

The check valve 6 is thus configured to close the slit 62 in response to an increase in the internal pressure of the elastic balloon 2 and the communication channel 4 to prevent outflow of the air from the elastic balloon 2 and communication channel 4 and to open the slit 62 in response to a reduction in the internal pressure of the elastic balloon 2 and the communication channel 4 to allow a fluid to enter the elastic balloon 2 and the communication channel 4 from the outside.

As shown in FIGS. 2, 3 and 5, the cylindrical member 60 of the check valve 6 is pressed by a push plate 63.

The push plate 63 is provided with a hole 63A that receives the cylindrical portion 51 of the pressure detector 5 and a communication hole 63B that is in communication with an inner space of the check valve 6.

Figure 7:
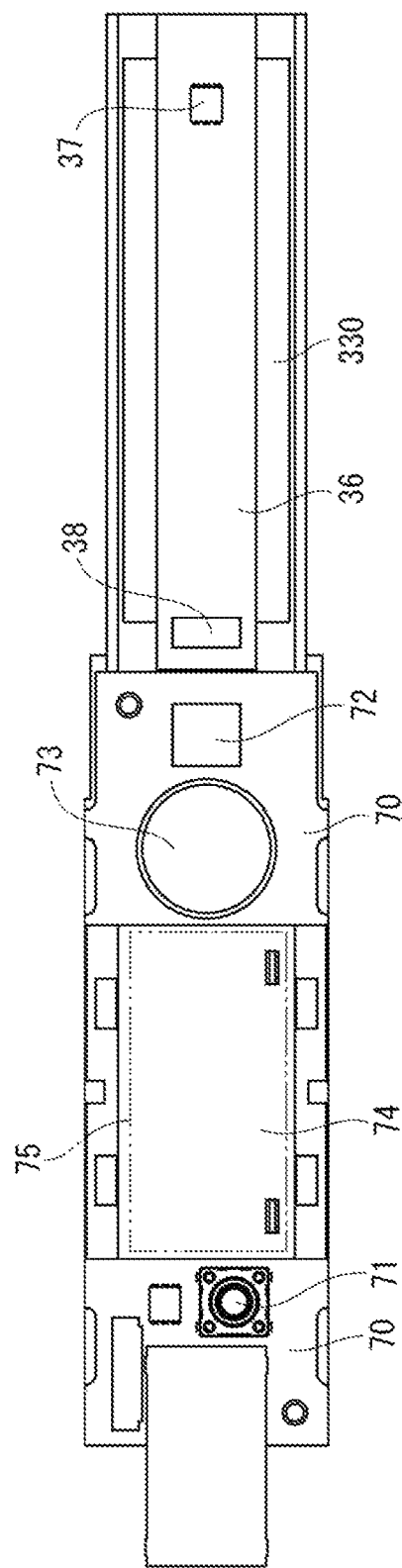
FIG. 7 is a front view showing an internal structure of the device body.
Figure 8:
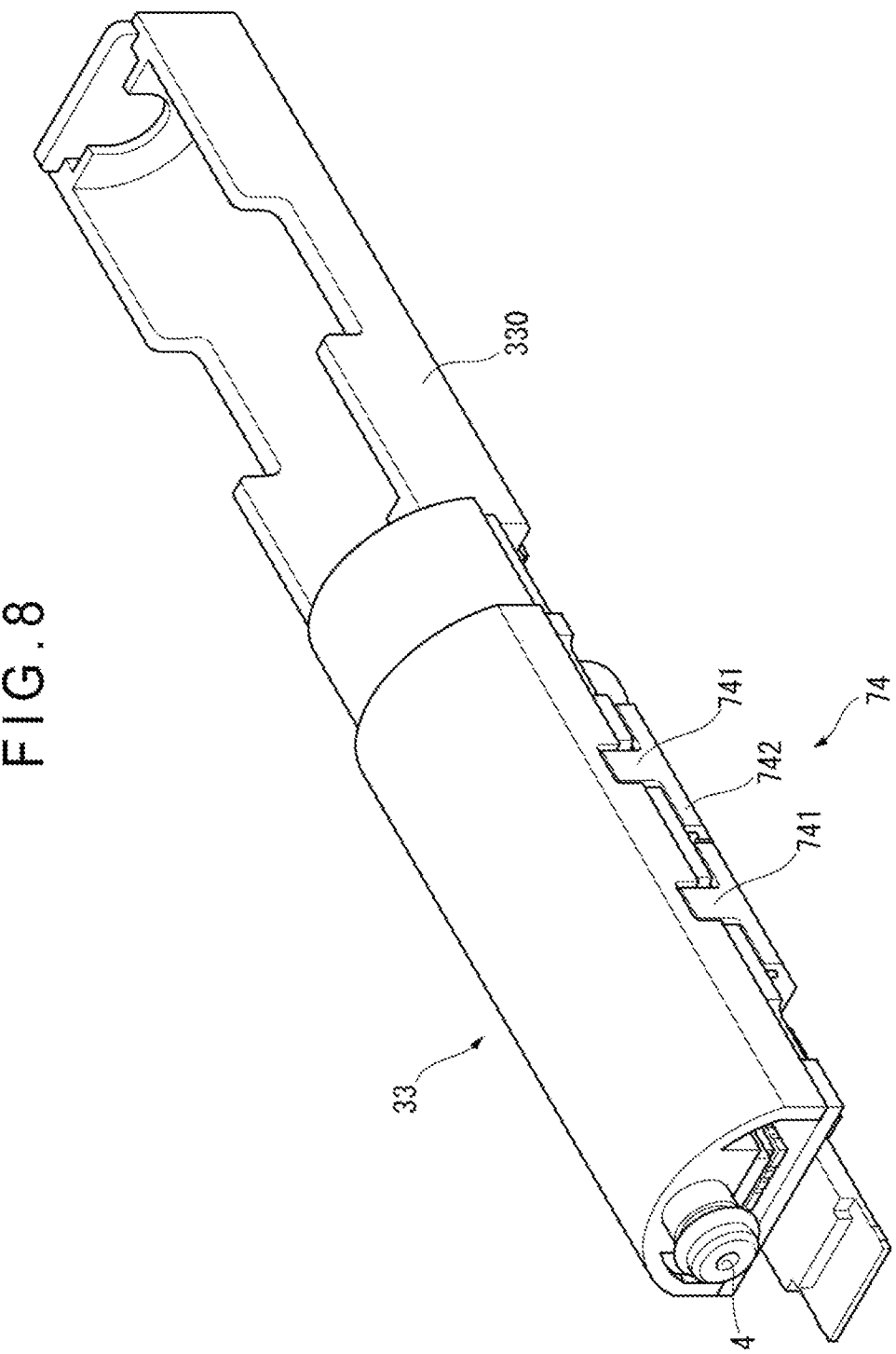
FIG. 8 is a perspective view showing the internal structure of the device body.
Figure 9:
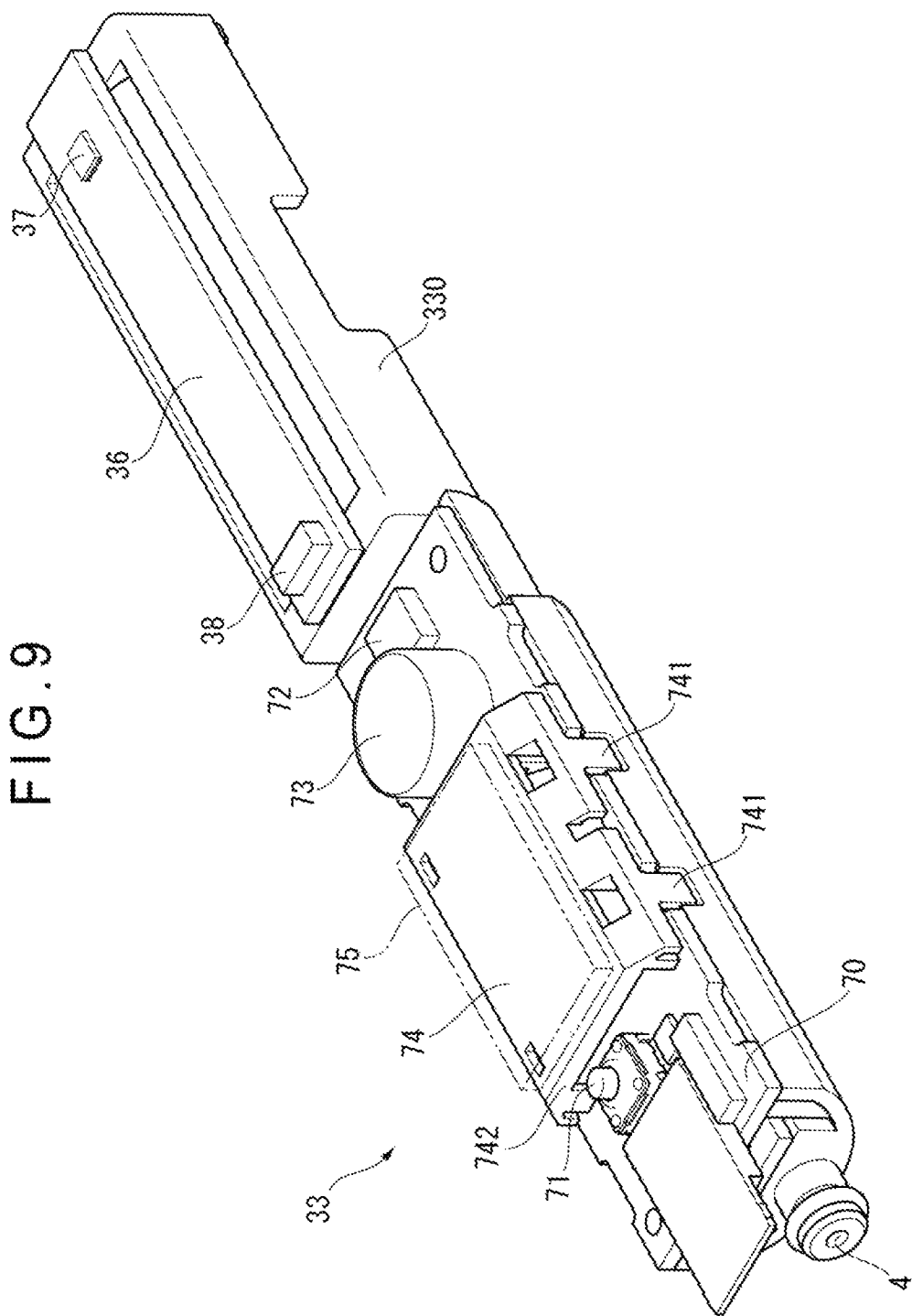
FIG. 9 is a perspective view showing the internal structure of the device body.

FIGS. 7 to 9 show an arrangement of the electronic component unit 7.

As shown in FIGS. 2, 3, 5, 7, 8 and 9, the electronic component unit 7 includes a circuit board 70 attached to the inner case 33, components provided to the circuit board 70, such as a switch 71, a connector 72, an electronic component (not shown), a buzzer 73 and an attachment member 74, and a display 75 mounted on the attachment member 74.

The diaphragm 52 of the pressure detector 5 is in close contact with a flat surface of the circuit board 70. A signal detected by the diaphragm 52 is sent to the electronic component through the circuit board 70.

The switch 71 is configured to start the electronic component unit 7. The electronic component unit 7 is installed in the inner case 33, and then front case 31 and the rear case 32 are attached.

The buzzer 73, which is configured to make a sound as lingual pressure information, is located near the attachment member 74.

The attachment member 74, which is a synthetic resin component, includes a plurality of legs 741 engaged on lateral faces of the circuit board 70 and a plate 742 integral with the legs 741. The display 75 is mounted on a flat surface of the plate 742. The display 75, which is a liquid crystal display (LCD) configured to digitally display a pressure value detected by the pressure detector 5, is electrically connected to the electronic component.

The pressure value displayed on the display 75 is recognized by a user through the window 313B of the front case 31.

The inner case 33A is provided at an opposite end thereof with a cavity 330 for housing a dry-cell battery V. Battery springs V1, V2 are located between walls of the cavity 330 and both ends of the dry-cell battery V (see FIG. 3).

An LED board 36 is located at a portion of the cavity 330 opposite to a portion where the dry-cell battery V is housed. The LED board 36 is provided with the color display LED 37 serving as an information output unit. The color display LED 37 is electrically connected to an electronic component (not shown) provided to the LED board 36.

The electronic component, which is also configured to control the driving of the color display LED 37, is electrically connected to the color display LED 37.

As shown in FIGS. 2 and 3, the ring-shaped case 34 includes a ring-shaped portion 341 and a plate-shaped portion 342 integral with the ring-shaped portion 341.

The ring-shaped portion 341 is provided with an air-intake filter 34A. The plate-shaped portion 342, which is configured to cover the LED board 36, is in an arc shape with the same curvature as that of the ring-shaped portion 341.

The plate-shaped portion 342 is provided with a window 34B that allows for transmission of light emitted from the color display LED 37. The window 34B faces a surface of the light-transmitting portion 325 facing the inside of the casing 3.

Figure 10:
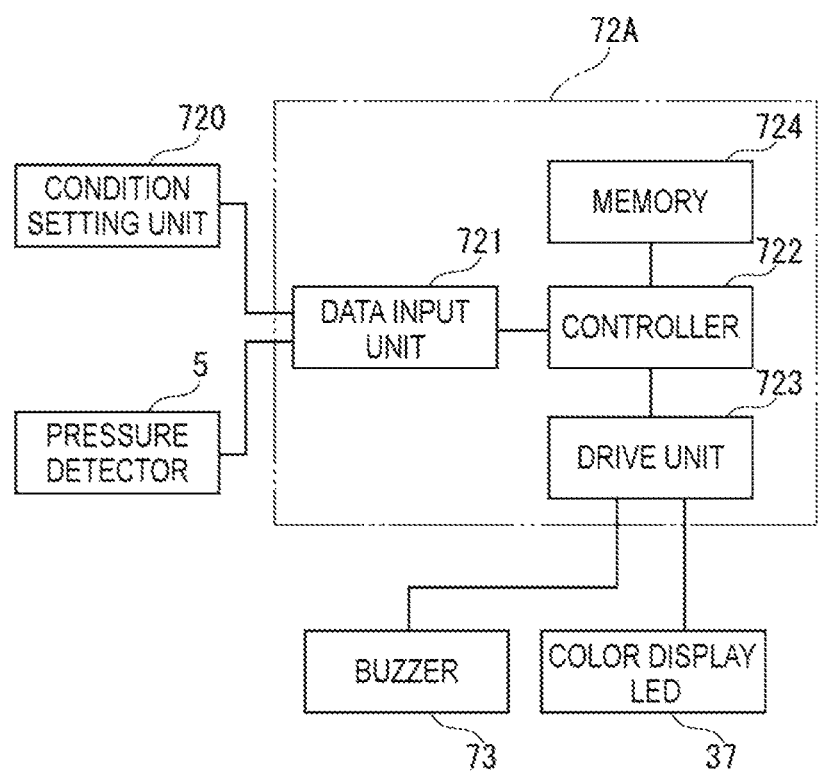
FIG. 10 is a block diagram of an electronic component.

FIG. 10 shows a circuitry of the electronic component.

As shown in FIG. 10, the electronic component includes a CPU 72A, which includes a data input unit 721 configured to receive the signal representing the pressure value from the pressure detector 5, a controller 722 configured to control the signal representing the pressure value inputted to the data input unit 721, a drive unit 723 configured to output a signal to the color display LED 37 and the buzzer 73 in response to a signal outputted from the controller 722, and a memory 724.

The controller 722 operates to display on the display 75 the pressure value detected by the pressure detector 5. The controller 722 sends to the drive unit 723 a signal for displaying the pressure value in blue on the color display LED 37 when the pressure value is equal to or more than a reference value, and sends to the drive unit 723 a signal for displaying the pressure value detected by the pressure detector 5 in red when the pressure value is less than the reference value. It should be noted that red and blue are colors opposite to each other. In the exemplary embodiment, colors other than red and blue, such as red and green and yellow and violet, may be used as long as these colors are opposite to each other. Further, the saturation of the colors may be controlled to change in response to the magnitude of the pressure value detected by the pressure detector 5. The controller 722 also sends to the drive unit 723 a signal for the buzzer 73 to make a sound having a pitch corresponding to the magnitude of the pressure value detected by the pressure detector 5. For instance, a sound having a pitch raised corresponding to the magnitude of the detected pressure value is made when the pressure value is equal to or more than the reference value, and no sound or only a small sound having a pitch lowered corresponding to the detected pressure value is made when the pressure value is less than the reference value.

Here, the reference value refers to a lingual pressure determined depending on the age and/or health condition of a user. A value equal to or more than the reference value indicates a normal state and a value less than the reference value indicates an abnormal state or occurrence of a problem. In the exemplary embodiment, a relationship between age and reference value and a relationship health condition, such as the level of need for care or support, and reference value are stored in the memory 724 in advance so that the reference value of lingual pressure is determined depending on an age and/or a health condition inputted using a condition setting unit 720.

The condition setting unit 720 includes an operation button (not shown) provided to the casing 3. An operation button(s) other than the condition setting unit 720, such as a power button, is also provided, and these buttons are arranged on an operation panel (not shown) provided on an outer circumferential surface of the casing 3.

It should be noted that the condition setting unit 720 and the memory 724 may be omitted in the exemplary embodiment.

Description will be made on an assembly method of the lingual pressure strengthening training device according to the exemplary embodiment.

First, the device body 1 is to be assembled. Specifically, as shown in FIG. 2, the check valve 6 and the O-ring 3L3 are set on the inner case 33 and the push plate 63 is attached to the inner case 33. Further, the filler plug 35 is attached to the inner case 33 with the screw 35C.

The battery springs V1, V2 are set in the cavity 330 of the inner case 33. Further, the circuit board 70 of the electronic component unit 7 and the LED board 36 are attached to the inner case 33.

The air-intake filter 34A is attached to the ring-shaped portion 341 of the ring-shaped case 34.

After being inserted in the ring-shaped case 34, the inner case 33 is set in the front case 31.

The dry-cell battery V is set in the cavity 330 of the inner case 33 and then the rear case 32 is attached.

The elastic balloon 2 is attached to the thus-assembled device body 1.

Description will be made on a method of performing a lingual pressure strengthening training while measuring a lingual pressure with the above lingual pressure strengthening training device.

First, a user, who holds the grip 30 of the casing 3 of the device body 1 by hand, inserts the balloon body 21 of the elastic balloon 2 between his or her palate and tongue and presses the balloon body 21 against his or her palate with his or her tongue.

The balloon body 21 is then deformed against its elasticity with its volume being reduced, increasing the internal pressure of the elastic balloon 2 and the communication channel 4. Air in the elastic balloon 2 and the communication channel 4 is thus to flow outside, but the slit 62 of the check valve 6 provided in the communication channel 4 is closed to prevent the outflow of the air from the elastic balloon 2 and the communication channel 4. Consequently, the pressure detector 5 detects the internal pressure of the elastic balloon 2 and the communication channel 4 that is in proportion to a pressing force applied by the tongue.

A signal representing a pressure value detected by the pressure detector 5 is sent to the controller 722 via the data input unit 721 of the CPU72A. The controller 722 then sends a signal to the drive unit 723, and the drive unit 723 drives the display 75 to digitally display the pressure value. The user can see the digitally displayed pressure value through the window 313B.

When the pressure value is equal to or more than the reference value, the color display LED 37 emits blue light. The blue light from the color display LED 37 can be seen through the light-transmitting portion 325 of the rear case 32. Further, the buzzer 73 makes a high-pitch sound.

When the user stops pressing the balloon body 21 with his or her tongue, the elastic balloon 2 is elastically deformed and restored to its original shape.

If pressure reduction, leakage or the like due to a change in temperature lowers the internal pressure of the elastic balloon 2 and the communication channel 4 to be a negative pressure, the slit 62 of the check valve 6 will be opened to let outer air into the elastic balloon 2 and the communication channel 4.

When the user again presses the balloon body 21 of the elastic balloon 2 with his or her tongue after stopping pressing the balloon body 21 with his or her tongue, the volume of the balloon body 21 is reduced as described above, increasing the internal pressure of the elastic balloon 2 and the communication channel 4. The pressure detector 5 detects the internal pressure of the elastic balloon 2 and the communication channel 4 in proportion to the pressing force applied by the tongue. When the pressure value detected by the pressure detector 5 is less than the reference value, the color display LED 37 emits a red light and the buzzer 73 makes a low-pitch sound or no sound.

The user will more forcefully press the balloon body 21 with his or her tongue while checking the blue light of the color display LED 37 and hearing the high-pitch sound from the buzzer 73.

Such a motion is repeated to perform the lingual pressure strengthening training.

The exemplary embodiment provides the following advantages.

(1) The controller 722 converts the pressure value detected by the pressure detector 5 into visual and aural lingual pressure information changed depending on the magnitude of the pressure value, and the information output unit, such as the buzzer 73 and the color display LED 37, outputs the lingual pressure information in response to a signal from the controller 722. The information output unit thus outputs different lingual pressure information depending on the pressing force applied on the elastic balloon 2 by the tongue, allowing users such as patients and elderly people to continue the training without being bored.

(2) The lingual pressure information is represented by color. Such color, which is outputted by the information output unit, is changed depending on the pressing force applied on the elastic balloon 2 by the tongue, making the lingual pressure visually recognizable. Such a change in color allows users, especially hearing-impaired users, to train while having fun.

(3) Red and blue, which are opposite colors to each other, are used as the lingual pressure information. The controller 722 controls the information output unit or the color display LED 37 to emit a blue light, which has an impression of "safety", when the pressure value detected by the pressure detector 5 is equal to or more than the reference value, and controls the color display LED 37 to emit a red light, which has an impression of "danger", when the pressure value detected by the pressure detector 5 is less than the reference value. The user is thus motivated to press the elastic balloon 2 so that a blue light is emitted, thereby efficiently strengthening the lingual pressure.

(4) The lingual pressure information is also represented by sound. Such sound, which is outputted by the buzzer 73, is changed depending on the pressing force applied on the elastic balloon 2 by the tongue, making the lingual pressure aurally recognizable. Such a change in sound allows users, especially blind users, to train while having fun.

(5) The controller 722 controls the buzzer 73 to make a sound whose pitch is raised in proportion to the pressure value detected by the pressure detector 5. The sound can thus be melodiously changed depending on the pressing force applied on the elastic balloon 2 by the tongue, allowing patients or elderly people to continue the lingual pressure strengthening training without being bored.

(6) The light-transmitting portion 325, which allows light emitted from the color display LED 37 to be externally visible, is located at a position corresponding to the projection 323A of the casing 3. The user can easily see the light transmitted through the light-transmitting portion 325 when holding the casing 3 by hand.

(7) The pressure detector 5 and the check valve 6 are located in the communication channel 4 that communicates with the elastic balloon 2. The check valve 6 prevents the outflow of air from the elastic balloon 2 and the communication channel 4 when the elastic balloon 2 is deformed to increase the internal pressure of the elastic balloon 2 and the communication channel 4, and lets outer air into the elastic balloon 2 and the communication channel 4 when the elastic balloon 2 is restored to its original shape to reduce the internal pressure of the elastic balloon 2 and the communication channel 4. Consequently, the pressure detector 5 detects the internal pressure of the elastic balloon 2 and the communication channel 4 that is in proportion to a pressing force applied by the tongue. When the user stops pressing the elastic balloon 2 with his or her tongue, the elastic balloon 2 is elastically restored to its original shape. Even when the internal pressure of the elastic balloon 2 and the communication channel 4 is lowered to be a negative pressure, the check valve 6 lets outer air into the elastic balloon 2 and the communication channel 4, thereby restoring the elastic balloon 2 to its original shape. Accordingly, the exemplary embodiment does not require solenoid valve and pump, which are typically used, and thus allows for reducing the weight of the lingual pressure measuring device and reducing production costs as compared with a typical device.

(8) The check valve 6, which is in the form of a duckbill valve, includes the pair of slant lips 61 that converge from the base ends toward the distal ends thereof, and the slit 62 provided to the abutting surfaces at the distal ends of the slant lips 61. Such a duckbill valve, which itself has a simple structure, contributes to further reducing the production costs of the device as a whole.

(9) The circuit board 70 and the pressure detector 5 are in close contact with each other without any unnecessary space therebetween, which results in making the device compact as a whole.

(10) The communication channel 4 includes the first channel 41 having the end opened to the pressure detector 5, and the second channel 42 having the end connected to the first channel and provided with the check valve. The pressure detector 5 and the check valve 6 are installed in the different channels and thus installation of these members in the channels can be facilitated.

(11) The second channel 42 has the opposite end opened to the inner space of the front case 31 and the rear case 32 through the check valve 6, so that air in the front case 31 and the rear case 32 enters the communication channel 4 through the check valve 6. Thus, as long as the front case 31 and the rear case 32 have a water-proof structure, water can be prevented from accidentally entering the communication channel 4.

(12) The device body 1 and the elastic balloon 2 are detachably attached to each other, allowing for easily stowing the device and replacing the elastic balloon 2 alone. The elastic balloon 2 may thus be replaced for each user. Such replacement is sanitarily favorable and reduces costs as compared with the case where the elastic balloon is replaced along with the device body.

(13) The large-diameter hole 33B, which serves as the tank, is in communication with the communication channel 4. Air from the inside of the elastic balloon 2 can thus be kept not only in the communication channel 4 but also in the large-diameter hole 33B, allowing for easily regulating the internal pressure of the communication channel 4.

Incidentally, it should be understood that the scope of the invention is not limited to the above-described exemplary embodiment(s) but includes modifications and improvements as long as an object of the invention is achievable.

For instance, the exemplary embodiment employs the check valve 6, which is located in the communication channel 4 that communicates with the elastic balloon 2, configured to prevent the outflow of air from the elastic balloon 2 and the communication channel 4 when the elastic balloon 2 is deformed to increase the internal pressure of the elastic balloon 2 and the communication channel 4, and to let outer air into the elastic balloon 2 and the communication channel 4 when the elastic balloon 2 is restored to its original shape to reduce the internal pressure of the elastic balloon 2 and the communication channel 4. However, the check valve may be replaced by a solenoid valve or an electric motor according to the invention. Even when the check valve is used, the check valve is not necessarily a duckbill valve but may alternatively be any other valve such as an umbrella valve including an umbrella-shaped member and a combination valve.

Further, although the exemplary embodiment employs the controller 722 that converts the pressure value detected by the pressure detector 5 into visual and aural lingual pressure information changed depending on the magnitude of the pressure value, and the information output unit, such as the buzzer 73 and the color display LED 37, that outputs the lingual pressure information in response to the signal from the controller 722, the lingual pressure information may be represented by number, letter or symbol in place of color and sound. For instance, a number(s) indicating the pressure value shown on the display 75 may be changed in size depending on the magnitude of the pressure value or, alternatively, a symbol(s) shown on the display 75 may be changed in size depending on the magnitude of the pressure value. The color display LED 37 may display letter, symbol and/or graphic in place of the display 75.

Further, even when the color display LED 37 is used, the color of light emitted from the color display LED 37 may be different from red or blue and thus may be yellow, green or any other color. Further, the color display LED 37 may emit a red or blue light only. In this case, the luminance of the light may be changed depending on the pressure value. Further, when sound is used, the loudness of the sound may be changed depending on the pressure value.

Further, although the large-diameter hole 33B is in communication with the communication channel 4 to serve as the tank, the large-diameter hole 33B may be omitted according to the invention.

Further, a spacer may be provided between the circuit board 70 and the pressure detector 5 while these components are connected to each other through a cable.

Further, although the casing 3 is provided with the projection 323A in the exemplary embodiment, the casing 3 may have a cylindrical contour according to the invention.

The entire disclosure of Japanese Patent Application No. 2015-074602, filed Mar. 31, 2015 is expressly incorporated by reference herein.

The invention claimed is:

1. A lingual pressure strengthening training device comprising:
   an elastic balloon configured to be inserted in a mouth of a patient;
   a pressure detector configured to detect an internal pressure of the elastic balloon;
   a controller configured to convert a pressure value detected by the pressure detector into at least one of visual lingual pressure information and aural lingual pressure information, the at least one of visual lingual pressure information or aural lingual pressure information being variable depending on the pressure value;
   a display and/or a buzzer configured to output the at least one of visual lingual pressure information and aural lingual pressure information in response to a signal from the controller;
   a memory storing in advance relationships between age of a patient and reference values of lingual pressure and relationships between a health condition indicating a level of a need for care and/or support and the reference values; and
   a condition setting unit configured to receive an input of the age of the patient and the health condition of the patient;
   wherein the controller is configured to select a reference value from the memory according to the age and health condition input into the condition setting unit, to compare the pressure value detected by the pressure detector with the selected reference value, to convert the detected pressure value into the at least one of visual lingual pressure information or aural lingual pressure information based on the comparison, and to use the at least one of visual lingual pressure or aural lingual pressure information to indicate one of a normal lingual state and an abnormal lingual state with the display and/or buzzer.

2. The lingual pressure strengthening training device according to claim 1, wherein the at least one of visual lingual pressure information or aural lingual pressure information is represented by one of two colors.

3. The lingual pressure strengthening training device according to claim 2, wherein
   the two colors consist of a first color and a second color that is opposite to the first color, and
   the controller is configured to control the display to display the first color when the pressure value detected by the pressure detector is equal to or more than the reference value, and to display the second color when the pressure value detected by the pressure detector is less than the reference value.

4. The lingual pressure strengthening training device according to claim 1, wherein the at least one of visual lingual pressure information or aural lingual pressure information is represented by a sound.

5. The lingual pressure strengthening training device according to claim 4, wherein the controller is configured to control the buzzer to make the sound with a pitch increased in proportion to the pressure value detected by the pressure detector.

6. A lingual pressure strengthening training method comprising:
   inserting an elastic balloon in a mouth of a patient;
   pressing the elastic balloon with a tongue of the patient;
   detecting an internal pressure of the pressed elastic balloon with a pressure detector;
   storing in advance, in a memory, relationships between age of a patient and reference values and relationships between a health condition indicating a level of need for care and/or support and the reference values;
   inputting the age and the health condition of the patient into a condition setting unit; and with a controller;
   selecting a reference value from the memory according to the input age and health condition;
   comparing a pressure value detected by the pressure detector with the selected reference value;
   determining at least one of visual lingual pressure information or aural lingual pressure information based on the comparison;
   outputting the at least one of visual lingual pressure information or aural lingual pressure information with a display and/or a buzzer, the at least one of visual lingual pressure information or aural lingual pressure information being changed depending on a magnitude of the pressure value detected by the pressure detector; and
   indicating, with the display and/or buzzer, one of a normal lingual state and an abnormal lingual state based on the at least one of visual lingual pressure information or aural lingual pressure information.

* * * * *